United States Patent
Lang et al.

(10) Patent No.: US 9,373,238 B2
(45) Date of Patent: Jun. 21, 2016

(54) MULTI-CHANNEL ASPIRATED SMOKE DETECTOR

(71) Applicant: Honeywell International Inc., Morristown, NJ (US)

(72) Inventors: Scott R. Lang, Geneva, IL (US); Bruce Robert Griffith, Geneva, IL (US)

(73) Assignee: HONEYWELL INTERNATIONAL INC., Morristown, NJ (US)

( * ) Notice: Subject to any disclaimer, the term of this patent is extended or adjusted under 35 U.S.C. 154(b) by 333 days.

(21) Appl. No.: 13/946,594

(22) Filed: Jul. 19, 2013

(65) Prior Publication Data

US 2015/0022363 A1    Jan. 22, 2015

(51) Int. Cl.
- G08B 17/10 (2006.01)
- *G06F 1/00* (2006.01)
- *A61B 1/00* (2006.01)
- *G08B 21/12* (2006.01)

(52) U.S. Cl.
CPC . G08B 17/10 (2013.01); *A61B 1/00* (2013.01); *G06F 1/00* (2013.01); *G08B 21/12* (2013.01)

(58) Field of Classification Search
CPC .................................. G06F 1/00; A61B 1/00
See application file for complete search history.

(56) References Cited

U.S. PATENT DOCUMENTS

| | | | | |
|---|---|---|---|---|
| 6,195,003 B1* | 2/2001 | Ichikawa | ............. | G08B 26/001 340/505 |
| 2010/0319465 A1* | 12/2010 | Ajay | ....................... | G01F 1/662 73/861.28 |
| 2013/0008787 A1* | 1/2013 | Mammoto | ............. | G08B 17/10 204/407 |

FOREIGN PATENT DOCUMENTS

| | | |
|---|---|---|
| EP | 2 224 406 A1 | 9/2010 |
| WO | WO 97/42486 A1 | 11/1997 |
| WO | WO 03/069571 A1 | 8/2003 |
| WO | WO 2006/050569 A1 | 5/2006 |

OTHER PUBLICATIONS

Extended European search report for corresponding EP application 14175491.1, dated Jan. 26, 2015.

* cited by examiner

*Primary Examiner* — Shirley Lu
(74) *Attorney, Agent, or Firm* — Husch Blackwell LLP

(57) ABSTRACT

An aspirated smoke detector includes a manifold coupled to a smoke sensing chamber of the smoke detector. The manifold couples ambient smoke from a plurality of locations to the smoke sensing chamber. A location of the origin of the smoke can be determined by associating a member of a plurality of a different type of smoke sensor with each of the locations. When smoke is detected in the sensing chamber, the members of the plurality can be interrogated to determine the location of the origin of the smoke in the sensing chamber.

17 Claims, 2 Drawing Sheets

MULTI-CHANNEL ASPIRATED SMOKE DETECTOR

FIELD

The application pertains to smoke detectors. More particularly, the application pertains to aspirated smoke detectors which receive smoke samples from a plurality of locations.

BACKGROUND

Some commercial installations for aspirated smoke detectors require a larger area of coverage than single channel products are capable of meeting. In order to cover a larger area, a multichannel smoke detector is needed. For cost purposes, it is desirable to only use one smoke sensing chamber. But, if air is being sampled from multiple pipes to the one chamber, the user still needs to know which pipe (channel) the smoke came from. This can be done mechanically via valves and actuators, but this is complex, slow, and expensive.

DETAILED DESCRIPTION

Figure 1:
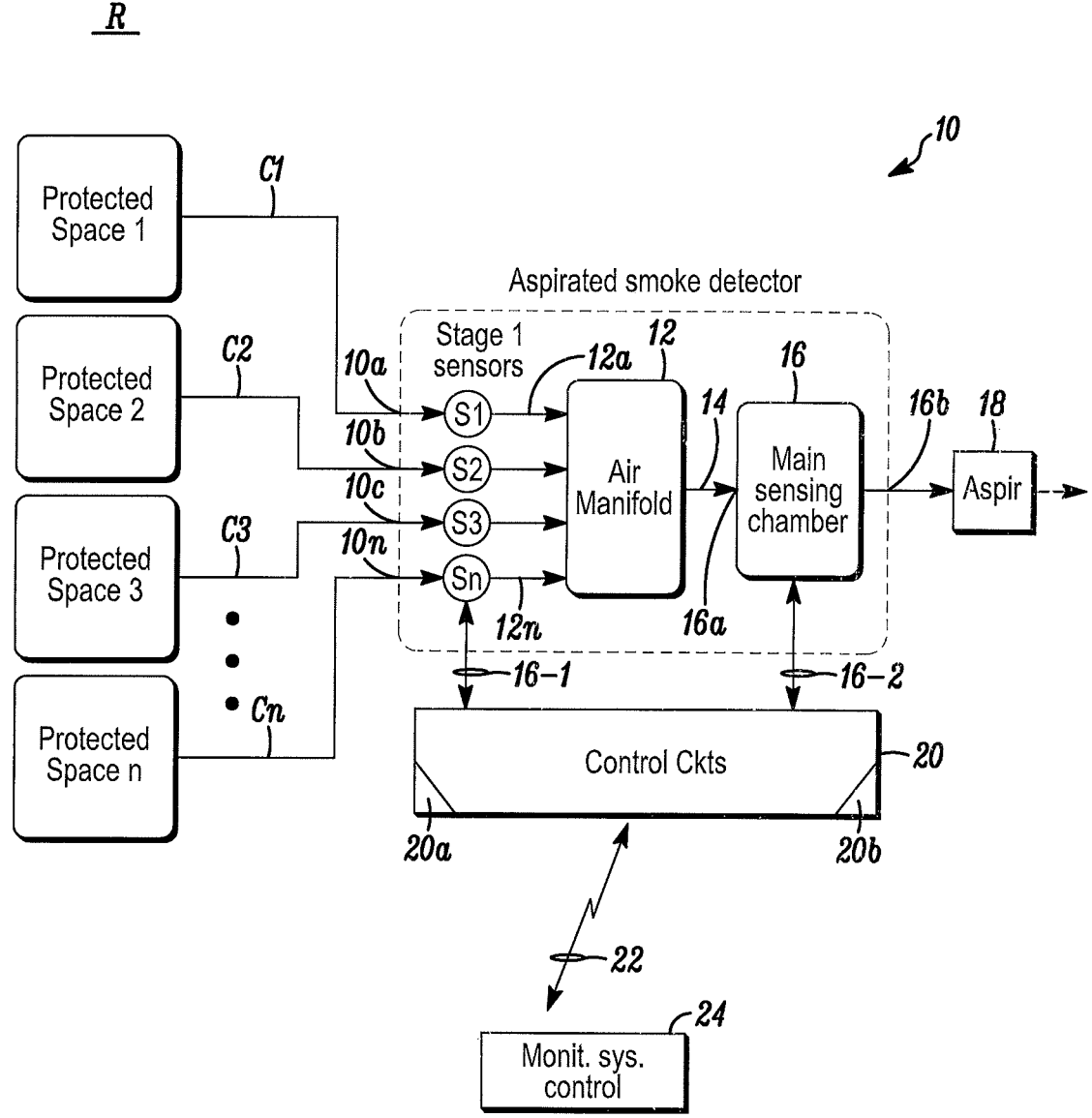
FIG. 1 is block diagram illustrating aspects of an embodiment hereof.

While disclosed embodiments can take many different forms, specific embodiments hereof are shown in the drawings and will be described herein in detail with the understanding that the present disclosure is to be considered as an exemplification of the principles hereof, as well as the best mode of practicing same, and is not intended to limit the claims hereof to the specific embodiment illustrated.

In accordance herewith, electronic gas or smoke sensing, on a per channel basis, can be combined with a common smoke chamber which receives smoke from multiple, different locations. Multiple ambient condition sensors, such as gas or smoke sensors, can be coupled to a manifold that combines multiple ambient air inflow channels to a single out flow that enters the smoke sensing chamber.

The ambient condition sensors can be activated after smoke is detected by the sensing chamber in order to determine, electrically, which input is the source of the detected smoke. By way of example only, and not limitation, a metal oxide semiconductor gas sensor can be coupled to each of the inflow channels. Those of skill will understand that other types of gas or smoke sensors come within the spirit and scope hereof. For example, electro-chemical gas sensors, photoelectric smoke sensors or the like, all without limitation, could also be used.

Metal oxide gas sensors are cross sensitive to a variety of gases that are produced by a range of fire types and are not subject to false alarm due to dust. They can be activated after the smoke chamber detects smoke. As a result, less signal processing is needed and power consumption is reduced.

Metal oxide gas sensors are typically available in TO-type packaging that can be fitted into a hole in the sampling tube or manifold. For example, a four channel device would use one smoke sensing chamber and four MOS gas sensors fitted to a four-to-one manifold.

FIG. 1 illustrates an aspirated smoke detector 10 which monitors smoke conditions in a plurality of different Protected Spaced, 1, 2, 3 . . . n of a region R. The Spaces 1, 2, 3 . . . n are coupled to the detector 10 via a plurality of conduits, or pipes, C1, C2, C3 . . . Cn. Each of the conduits or pipes Ci has an inflow port located in or adjacent to a respective one of the Spaces 1, 2, 3 . . . n.

Each of the conduits or pipes Ci is coupled to a respective inflow port 10a, b, c . . . n of the detector 10. Each of the inflow ports 10i is coupled to a respective Stage 1 ambient condition sensor, such as a gas or smoke sensor Si. The particular details of the sensors Si are not a limitation hereof. Sensor Si can be continuously or intermittently energized without limitation. Each of the sensors Si is coupled by a respective pipe or conduit to a manifold 12.

Manifold 12 combines each of the n inflow conduits, such as 12a, 12b . . . 12n to a single output flow conduit, or pipe 14 which is in turn coupled to an inflow port 16a of main sensing chamber 16. Ambient air, which might be carrying smoke or gas of interest, flows from manifold 12, via conduit 14 into chamber 16, where a gas or smoke sensing process can be carried. That air exits chamber 16, via outflow port 16b and an aspirator 18.

Control circuits 20, of the detector 10, are coupled to each of the Stage 1 sensors Si via cables 16-1, as well as to the main sensing chamber 16 by cables 16-2. Control circuits 20 can implement gas and/or smoke processing as in exemplary method 100 discussed subsequently. Control circuits 20 could be implemented, at least in part, via a programmable processor 20a and local control software 20b.

Control circuits 20 can communicate via a wired or wireless medium 22 with a displaced monitoring system control unit 24. It will be understood that details of the control unit 24 are not limitations hereof.

Figure 1A:
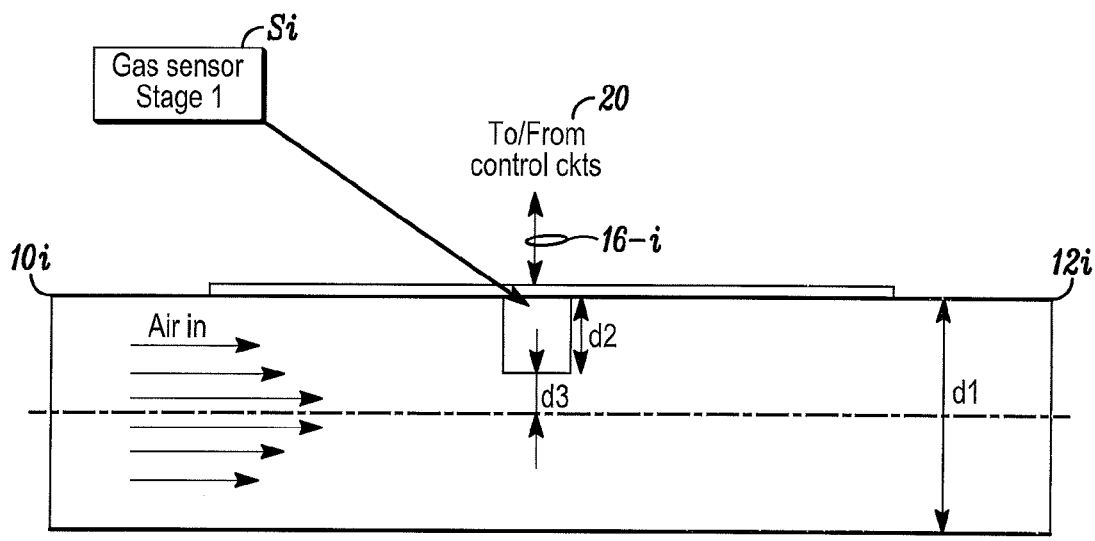
FIG. 1A is a side view, partly in section illustrating other aspects of the embodiment of FIG. 1.

FIG. 1A illustrates a gas sensor Si coupled via cable 16-i to control circuits 20. Sensor Si is attached to conduit 12i which has a diameter d1. Those of skill will understand that diameter d1 is selected in accordance with a height dimension d2 of sensor Si to provide an appropriate flow dimension d3 for the inflowing atmospheric air from the respective Protected Space i.

Figure 2:
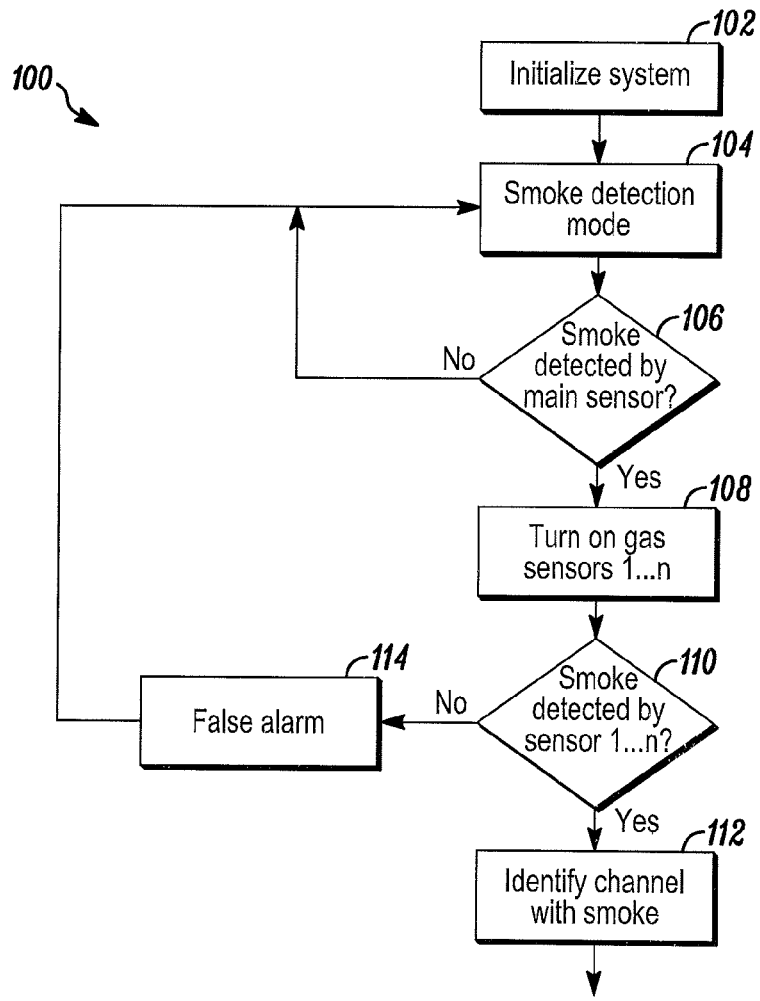
FIG. 2 is a flow diagram illustrating a method in accordance herewith.

FIG. 2 illustrates a flow diagram of a method 100 of operating detector 10. The system of detector 10 can be initialized as at 102. It can be placed in a smoke detection mode, as at 104. If smoke is detected in main sensing chamber 16, as at 106, outputs from all of the Stage 1 gas or smoke sensors Si are read as at 110. If not on, they can be first turned on as at 108.

Control circuits 20 can determine which of the sensors Si are detecting gas or smoke, as at 110. The conduit or pipe, Ci through which the gas or smoke is flowing can then be identified. This in turn specifies the Protected Space i from which the gas, or smoke is being drawn. Circuits 20 can then emit an appropriate alarm indictor to the control unit 24.

From the foregoing, it will be observed that numerous variations and modifications may be effected without departing from the spirit and scope of the invention. It is to be understood that no limitation with respect to the specific apparatus illustrated herein is intended or should be inferred. It is, of course, intended to cover by the appended claims all such modifications as fall within the scope of the claims.

Further, logic flows depicted in the figures do not require the particular order shown, or sequential order, to achieve desirable results. Other steps may be provided, or steps may be eliminated, from the described flows, and other components may be added to, or removed from the described embodiments.

The invention claimed is:

1. An aspirated smoke detector comprising:
   a smoke sensing chamber with a fluid flow input port and a fluid flow output port;
   a manifold having a first plurality of input ports, and an output port where the output port is coupled to the fluid flow input port of the sensing chamber;
   a second plurality of ambient condition sensors where each member of the second plurality is associated with a member of the first plurality; and
   control circuits;
   wherein the control circuits are coupled to a smoke indicating output from the smoke sensing chamber,
   wherein the control circuits are coupled to each ambient condition sensor in the second plurality, and
   wherein the control circuits, in response to a smoke indication signal from the smoke indicating output, evaluate output from each of the ambient condition sensors in the second plurality to determine which of the first plurality of input ports is a source of sensed smoke in the sensing chamber.

2. A detector as in claim 1 further comprising a third plurality of inflow pipes, wherein an inflow pipe of the third plurality is coupled to each member of the first plurality of input ports.

3. A detector as in claim 2 further comprising an ambient condition sensor of the second plurality attached to each inflow pipe of the third plurality, or each inflow port of the first plurality.

4. A detector as in claim 3 wherein the control circuits, in response to the smoke indication signal, cycle through the second plurality of ambient condition sensors to determine which of the third plurality of inflow pipes is carrying the sensed smoke.

5. A detector as in claim 4 wherein the control circuits generate an alarm indicting electrical signal in response to the smoke indication signal from the sensing chamber.

6. A detector as in claim 3 wherein each of the ambient condition sensors in the second plurality is selected from a class which includes at least, semiconductor gas sensors, electrochemical gas sensors, photoelectric smoke sensors, or, ionization-type smoke sensors.

7. A detector as in claim 6 further comprising an aspirator coupled to the smoke sensing chamber.

8. A method comprising:
   establishing a plurality of confined smoke, or gas, conducting paths;
   establishing a common smoke sensing region coupled to each of the paths in the plurality;
   control circuits sensing a smoke condition in the region; and
   responsive to the control circuits sensing the smoke condition in the region, the control circuits electrically determining which of the paths in the plurality provided smoke to the region.

9. A method as in claim 8 wherein the control circuits determining which of the paths in the plurality provided the smoke to the region includes the control circuits sensing the smoke condition, or a gas condition, on each of the plurality of paths.

10. A method as in claim 9 further comprising coupling a separate smoke, or gas, sensor to each of the plurality of paths.

11. A method as in claim 10 wherein the control circuits sensing the smoke condition in the region includes the control circuits sensing the smoke in the region using a first smoke related characteristic.

12. A method as in claim 11 wherein the control circuits sensing the smoke condition, or the gas condition, on each of the paths in the plurality includes the control circuits sensing the smoke condition, or the gas condition, on each of the paths in the plurality using a second, ambient condition characteristic, different from the first smoke related characteristic.

13. A method as in claim 12 further comprising providing a common draw of the smoke on each of the paths in the plurality.

14. A method as in claim 13 further comprising coupling an aspirating unit to the region.

15. A method as in claim 10 further comprising evaluating electrical signals from the separate smoke, or gas, sensor coupled to each of the plurality of paths to determine a source of the smoke.

16. An aspirated smoke detector comprising:
   a manifold coupled to a smoke sensing chamber of the smoke detector;
   a plurality of channels coupled to the manifold for coupling ambient smoke from respective locations to the smoke sensing chamber; and
   a plurality of ambient condition sensors associated with respective ones of the locations,
   wherein, when the ambient smoke is detected in the smoke sensing chamber, each of the plurality of ambient condition sensors is interrogated to determine a location of origin of the ambient smoke in the smoke sensing chamber.

17. A detector as in claim 16 wherein each of the plurality of ambient condition sensors includes one of a solid state gas sensor, or an electrochemical gas sensor.

* * * * *